(12) United States Patent
Belcastro et al.

(10) Patent No.: US 9,061,300 B2
(45) Date of Patent: Jun. 23, 2015

(54) BENT CAPILLARY TUBE AEROSOL GENERATOR

(75) Inventors: Marc D. Belcastro, Glen Allen, VA (US); Jeffrey A. Swepston, Powhatan, VA (US)

(73) Assignee: Philip Morris USA Inc., Richmond, VA (US)

( * ) Notice: Subject to any disclaimer, the term of this patent is extended or adjusted under 35 U.S.C. 154(b) by 1141 days.

(21) Appl. No.: 12/002,773

(22) Filed: Dec. 19, 2007

(65) Prior Publication Data

US 2008/0156326 A1    Jul. 3, 2008

Related U.S. Application Data

(60) Provisional application No. 60/877,650, filed on Dec. 29, 2006.

(51) Int. Cl.
| | | |
|---|---|---|
| *A61M 15/00* | (2006.01) | |
| *H05B 3/00* | (2006.01) | |
| *B05B 1/24* | (2006.01) | |
| *A61M 11/04* | (2006.01) | |
| *B05B 17/04* | (2006.01) | |
| *A61M 16/00* | (2006.01) | |

(52) U.S. Cl.
CPC ............... *B05B 1/24* (2013.01); *A61M 11/041* (2013.01); *A61M 15/0065* (2013.01); *A61M 2016/0021* (2013.01); *A61M 2016/0027* (2013.01); *A61M 2202/064* (2013.01); *A61M 2205/8206* (2013.01); *B05B 17/04* (2013.01); *A61M 11/042* (2014.02)

(58) Field of Classification Search
CPC ............ A61M 11/041; A61M 11/042; A61M 15/0065; A61M 2016/0021; A61M 2016/0027; A61M 2202/064; A61M 2205/8206; B05B 17/04; B05B 1/24
USPC ......... 382/478; 219/200; 128/203.12, 128.27; 392/478
See application file for complete search history.

(56) References Cited

U.S. PATENT DOCUMENTS

| | | | | | |
|---|---|---|---|---|---|
| 2,931,358 | A | * | 4/1960 | Sheridan .................. | 128/207.18 |
| 3,726,275 | A | * | 4/1973 | Jackson et al. ........... | 128/207.18 |
| 4,406,283 | A | * | 9/1983 | Bir ............................ | 128/207.18 |
| 4,602,644 | A | * | 7/1986 | DiBenedetto et al. ........ | 600/538 |
| 5,046,491 | A | * | 9/1991 | Derrick .................... | 128/200.24 |
| 5,400,665 | A | * | 3/1995 | Zhu et al. ................... | 73/863.12 |

(Continued)

FOREIGN PATENT DOCUMENTS

WO    WO 2007/102087    9/2007

OTHER PUBLICATIONS

International Search Report and Written Opinion dated Aug. 28, 2008 for PCT/IB2007/004497.

(Continued)

*Primary Examiner* — Dana Ross
*Assistant Examiner* — Ket D Dang
(74) *Attorney, Agent, or Firm* — Buchanan Ingersoll & Rooney PC

(57) ABSTRACT

An apparatus for generating aerosol having a capillary tube, which includes at least one bend, fluid inlets, regions of reduced wall thickness located between the fluid inlets and the at least one bend, and an outlet along the at least one bend. The capillary tube is heated to a temperature sufficient to volatilize fluid in the capillary tube, such that the volatilized fluid discharges from the outlet to form an aerosol.

26 Claims, 6 Drawing Sheets

(56) References Cited

U.S. PATENT DOCUMENTS

| | | | |
|---|---|---|---|
| 5,706,389 A * | 1/1998 | Pohler | 392/397 |
| 5,743,251 A | 4/1998 | Howell et al. | |
| 6,491,233 B2 | 12/2002 | Nichols | |
| 6,568,390 B2 * | 5/2003 | Nichols et al. | 128/203.16 |
| 6,616,896 B2 * | 9/2003 | Labuda et al. | 422/84 |
| 6,640,050 B2 | 10/2003 | Nichols et al. | |
| 6,681,769 B2 | 1/2004 | Sprinkel, Jr. et al. | |
| 6,701,921 B2 | 3/2004 | Sprinkel, Jr. et al. | |
| 6,701,922 B2 | 3/2004 | Hindle et al. | |
| 6,715,487 B2 | 4/2004 | Nichols et al. | |
| 6,766,220 B2 | 7/2004 | McRae et al. | |
| 6,772,757 B2 | 8/2004 | Sprinkel, Jr. | |
| 6,804,458 B2 | 10/2004 | Sprinkel, Jr. et al. | |
| 6,854,461 B2 | 2/2005 | Nichols et al. | |
| 6,871,792 B2 | 3/2005 | Pellizzari | |
| 7,117,867 B2 | 10/2006 | Cox et al. | |
| 2003/0056790 A1 | 3/2003 | Nichols et al. | |
| 2003/0108342 A1 | 6/2003 | Sherwood et al. | |
| 2004/0016427 A1 * | 1/2004 | Byron et al. | 128/200.14 |
| 2004/0050383 A1 * | 3/2004 | Cox et al. | 128/200.14 |
| 2004/0084050 A1 * | 5/2004 | Baran | 128/207.14 |
| 2004/0194781 A1 * | 10/2004 | Fukunaga et al. | 128/203.12 |
| 2007/0262478 A1 | 11/2007 | Price et al. | |

OTHER PUBLICATIONS

International Preliminary Report on Patentability dated Aug. 14, 2008 for PCT/IB2007/001654.

International Preliminary Report on Patentability and Written Opinion mailed Jul. 9, 2009 for International Application No. PCT/IB2007/004497.

* cited by examiner

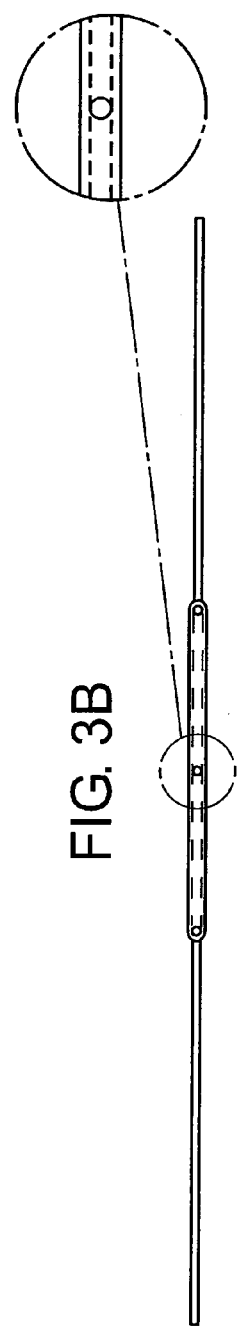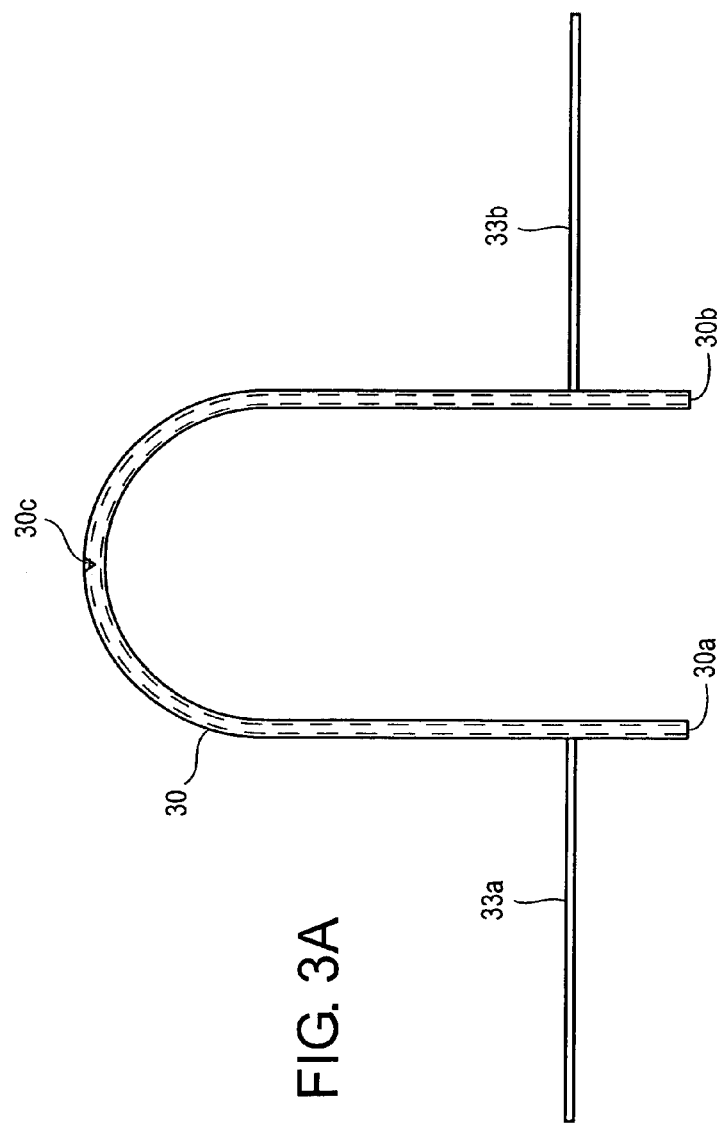

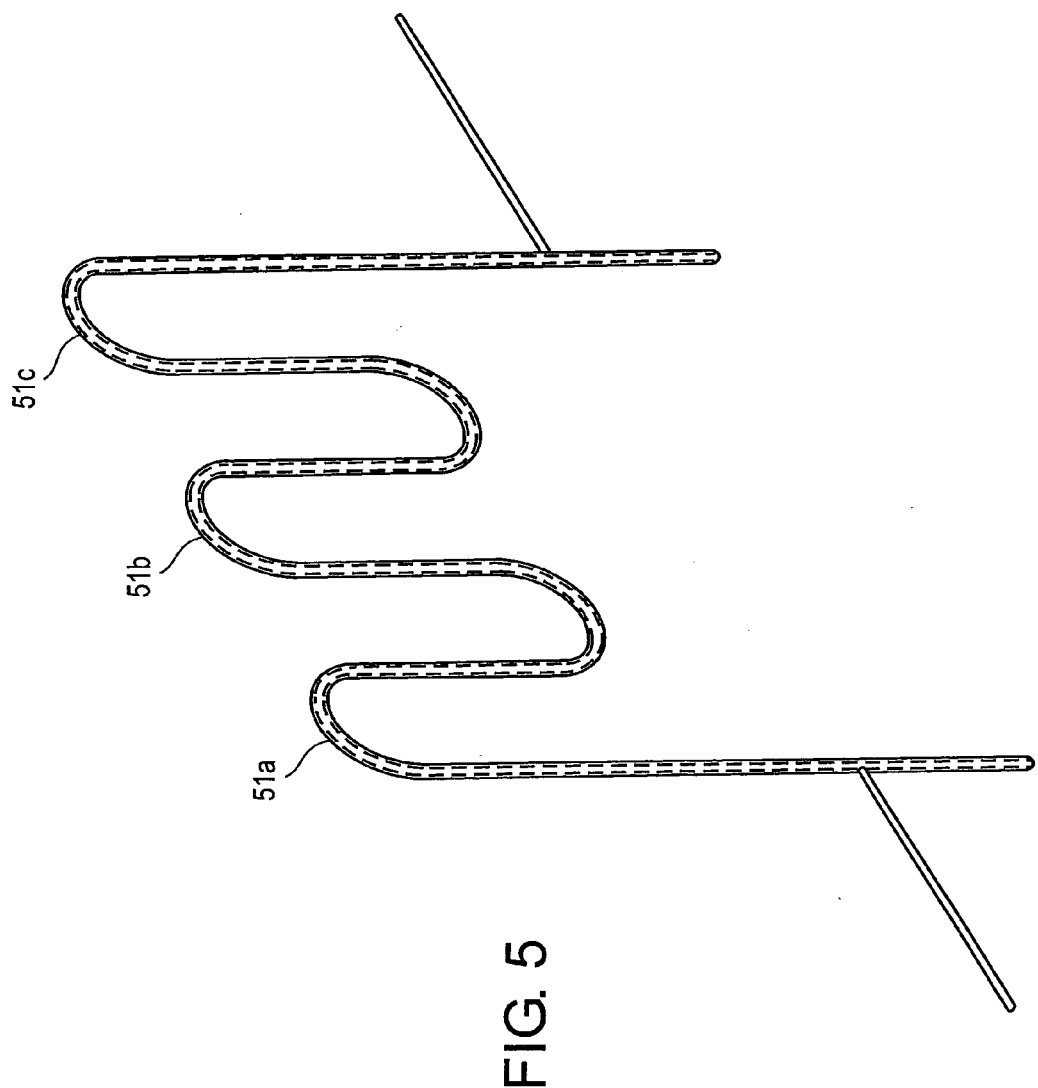

BENT CAPILLARY TUBE AEROSOL GENERATOR

CROSS REFERENCE TO RELATED APPLICATION

This application claims priority under 35 U.S.C. §119(e) to U.S. provisional Application No. 60/877,650, filed on Dec. 29, 2006, the entire content of which is incorporated herein by reference.

BACKGROUND

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into the lungs. Aerosols are also used for purposes such as providing desired scents to rooms, distributing insecticides and delivering paint and lubricant.

SUMMARY

Provided is an aerosol generator in the form of a capillary tube. The capillary tube includes at least one bend, fluid inlets, regions of reduced wall thickness located between the fluid inlets and the bend, and an outlet along the bend. Volatilized fluid expands out of the outlet and mixes with ambient air to form an aerosol. Electrical resistance is preferably increased in the regions of reduced wall thickness. The fluid inlets may be located at ends of the capillary tube. The capillary tube may comprise more than one bend, e.g., plural bends in the same plane or the tube may be coiled. The aerosol generator may include a source of liquid in fluid communication with the fluid inlets. The capillary tube may be 5 to 40 millimeters, preferably 10 to 25 millimeters, long and has an inner diameter of 0.1 to 0.5 millimeters, preferably 0.1 to 0.2 millimeters. The capillary tube may have a wall thickness of about 0.1 millimeters and the regions of reduced wall thickness may have a wall thickness of about 0.01-0.09 millimeters, preferably about 0.04 millimeters.

Also provided is an aerosol generator including a capillary tube. The capillary tube includes at least one bend, fluid inlets, regions of reduced wall thickness located between the fluid inlets and the at least one bend, an outlet along the at least one bend and a heating mechanism which heats the capillary tube to a temperature sufficient to volatilize fluid in the capillary tube. The capillary tube can be made of an electrically resistive heating material such as stainless steel, the electrical resistance is preferably increased in the regions of reduced wall thickness, and the heating mechanism can be a power supply with leads attached to the capillary tube to pass electrical current at least along the bend to heat the capillary tube to a temperature sufficient to volatilize fluid in the capillary tube. Preferably, the regions of reduced wall thickness are located between the leads and the bend. The aerosol generator may further comprise a mouthpiece and/or a source of fluid.

Further provided is a method for generating an aerosol. The method includes the steps of supplying fluid to an aerosol generator, which includes a capillary tube comprising at least one bend, first and second fluid inlets, regions of reduced wall thickness located between the fluid inlets and the bend, and an outlet along the bend, and heating the capillary tube to heat the fluid to a temperature sufficient to volatilize the fluid to form a volatized fluid, such that the volatilized fluid expands out of the outlet of the capillary tube. The volatilized fluid mixing with ambient atmospheric air to form an aerosol. The regions of reduced wall thickness may be formed by, for example, electro-polishing, centerless grinding, standard machining, chemical etching, or combinations thereof. The outlet is preferably equidistant from the first and second fluid inlets. Fluid may be supplied to the first and second fluid inlets at identical or different flow rates. Identical or different fluids, which may be liquids, may be supplied to the first and second fluid inlets. A liquid may be supplied to a first fluid inlet and a gas may be supplied to a second fluid inlet. Fluid supplied to the capillary tube may comprise tobacco extract, medicament, fuel, water, flavorant, and/or a carrier.

BRIEF DESCRIPTION OF THE DRAWINGS

FIG. 3 provides an enlarged view of the bent capillary tube, with FIG. 3a providing a front view, FIG. 3b providing a top view, and FIG. 3c providing a magnified view of the outlet of the capillary tube.

FIGS. 5 and 6 show additional embodiments of the bent capillary tube. The bent capillary tube of FIG. 5 includes multiple bends and the bent capillary tube of FIG. 6 includes a coiled tube having multiple bends.

DESCRIPTION OF THE PREFERRED EMBODIMENTS

Figure 1:
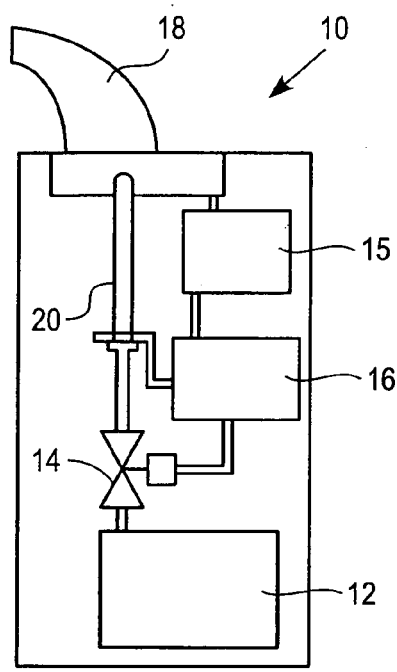
FIG. 1 is an illustration of a fluid vaporizing device.

Provided is a fluid vaporizing device useful for applications including aerosol generation. The device includes a bent (or "arcuate") capillary tube or passage which can be heated by passing electrical current therethrough, and through which fluid flows to be at least partially vaporized and if desired to generate an aerosol. Preferably, the bent capillary passage comprises an arcuate passage portion and an outlet at a location along the arcuate passage. In order to heat the tube, an electrical current, supplied by a first electrode at one inlet end of the tube, passes along the tube to a second electrode at the other inlet end of the tube. Fluid from the same or different sources can be supplied as a pressurized liquid at the inlets and is at least partially converted to a vapor by the input of heat generated by resistance heating from the flow of electricity along the tube as the fluid flows from the inlet ends through the tube toward the outlet. When used as an aerosol generator of an inhaler, such as a hand-held inhaler for aerosolizing medicaments or flavor substances, as the vapor exits from the tube at the outlet of the capillary tube an aerosol is produced as the vapor enters the surrounding atmosphere.

In a preferred embodiment, the bent capillary tube comprises at least one bend (curved or arcuate portion), such as a 180° bend. The outlet of the capillary tube is located at the bend, such that the inlet ends of the tube are equidistant from the outlet of the tube. Thus, as the bent capillary tube has more than one path (e.g., two legs) through which fluid travels from the inlet ends of the tube to the outlet, the bent capillary tube provides for a very compact structure compared to an aerosol generator comprising a linear capillary tube having a single path through which fluid travels from inlet to outlet. Further, compared to an aerosol generator comprising a capillary tube having a single path through which fluid travels from inlet to outlet, the pressure required to move fluid through the two legs of the bent capillary tube is lower to achieve a targeted flow rate. Conversely, for a targeted flow rate of aerosol, the flow rate of fluid traveling through each leg of the tube is slower. As a result of a slower flow rate of fluid traveling through the two legs of the tube, heat is transferred more efficiently from the tube into the fluid, less energy is required to vaporize liquid flowing through the tube and the footprint of the tube may be reduced.

As the bent capillary tube has more than one inlet, an aerosol comprising more than one fluid may be formed. More specifically, different liquids, which may not mix well, may be fed into respective inlet ends of the tube. Alternatively, an aerosol comprising liquid and gas may be formed by feeding liquid into, for example, one inlet end of the tube and gas into, for example, the other inlet end of the tube. Further, a carrier solution containing tobacco extracts or tobacco flavor constituents may be used to form an aerosol, with the resulting aerosol having taste attributes of tobacco smoke generated without combustion.

Preferably, the temperature of the tube and the fluid are greatest at the outlet and the outlet is at the center of the bend in the tube, (e.g., is equidistant from each inlet end of the tube as well as equidistant from each electrode). Preferably, the outlet has a diameter approximately equal to the inner diameter of the bent capillary tube. However, if different fluids are fed into each inlet end of the tube, in order to optimize aerosol generation, it may be preferable that the outlet not be equidistant from each inlet end of the tube or equidistant from each electrode and/or the electrode not be located in identical positions on respective paths from the inlet ends of the tube to the outlet. Further, if different fluids are fed into each inlet end of the tube, in order to optimize aerosol generation, it may be preferable that the different fluids be fed at different flow rates.

The capillary tube can be made entirely from an electrically conductive material, such as stainless steel, so that as a voltage is applied to a length of the tube, the tube is heated by the flow of electrical current through the tube, and the fluid passing through the tube is vaporized. As an alternative, the tube could be made from a non-conductive or semi-conductive material, such as glass or silicon, with a coating or layer of resistance heating material such as platinum for heating the tube. Specifically, the tube could be fused silica with heater element formed by a resistive coating.

In a preferred embodiment, the bent capillary tube may be described as having three regions: a region of the tube where only vapor exists, regions of the tube where at least some liquid exists, and transition regions where liquid is vaporized (located between the outlet and inlets). The outlet of the tube is preferably located in the region of the tube where sufficient vapor exists to produce a desired aerosol. Preferably, the regions of the tube where liquid enters the tube have reduced wall thickness, and interfaces between the regions of the tube having differing wall thicknesses may be found in the transition regions where both vapor and liquid exists. However, depending on the compound(s) from which aerosol is being formed, interfaces between the regions of the tube having differing wall thicknesses may be located closer to the outlet.

The lengths of the regions of reduced wall thickness can be selected to achieve a desired heating profile. As an example, for a capillary tube having one bend and length 18 to 20 millimeters from electrical lead to electrical lead, the length of each section of the capillary tube (from the outlet of the capillary tube to each electrical lead) is 9 to 10 millimeters, and within this length, the regions of reduced wall thickness may be 5 to 7 millimeters each.

Reduction of the wall thickness of the capillary tube in select regions increases the amount of heat energy transferred from the capillary tube to the fluid. Further, by reducing the wall thickness of the capillary tube in predetermined regions, the temperature gradient across the length of the capillary tube can be managed. Thus, heat energy may be delivered to the aerosol formation to form an aerosol quickly, while ensuring that the capillary tube does not exceed predetermined temperature limits in the region of the tube where less liquid is present. Additionally, by reducing the wall thickness of the capillary tube in predetermined regions, the amount of electrical energy required to raise the temperature of the capillary tube from ambient to operating temperature can be significantly reduced.

By reducing wall thickness, the electrical resistance is increased. As a result, less energy and time are required to heat the tube to the operating temperature. Any suitable fabrication technique for effectively reducing the outside diameter of the capillary tube may be employed. Such techniques include, for example, electro-polishing, centerless grinding, standard machining, chemical etching, and combinations thereof. Specifically, for a 30 gauge stainless steel capillary tube (about 0.3 millimeter outside diameter, about 0.1 millimeter inside diameter, and about 0.1 millimeter wall thickness), selected regions of the outside diameter of the capillary tube may be reduced by electro-polishing to about 0.2 millimeters outside diameter, leaving a wall thickness of about 0.04 millimeters.

As the capillary tube is heated to the operating temperature of the aerosol generator and liquid begins to flow through the tube, a given amount of energy is required to form an aerosol from the liquid. In the regions of the capillary tube where liquid exists and flows, a significant amount of heat energy is transferred from the interior wall of the capillary tube into the liquid. However, the amount of heat energy transferred from the interior wall of the capillary tube into the liquid in the bend is limited by the amount of energy absorbed by the liquid in forming the aerosol, with any excess heat remaining in the bend of the capillary tube. Thus, by locating the regions of reduced wall thickness prior to the bend, heating can be increased in those regions and the comparatively thicker wall of the bend allows for reduced electrical resistance in the bend as compared to the regions of reduced wall thickness, to provide a more uniform temperature gradient across the entire capillary tube.

FIG. 1 shows an embodiment of a fluid vaporizing device in the form of an aerosol generator 10 for use as a hand held inhaler. As shown, the aerosol generator 10 includes a source 12 of fluid, a valve 14, a heater arrangement comprising a bent capillary tube 20, a mouthpiece 18, an optional sensor 15 and a controller 16. The controller 16 includes suitable electrical connections and ancillary equipment such as a battery which cooperates with the controller for operating the valve 14, the sensor 15 and supplying electricity to heat the bent capillary tube 20. In operation, the valve 14 can be opened to allow a desired volume of fluid from the source 12 to enter the bent capillary tube 20 prior to or subsequent to detection by the sensor 15 of a pressure drop in the mouthpiece 18 caused by a person drawing (inhaling) upon the aerosol generator 10. As fluid is supplied to the bent capillary tube 20, the controller 16 controls the amount of power provided to heat the capillary tube sufficiently to volatilize fluid in the bent capillary tube 20, i.e., the controller 16 controls the amount of electricity passed through the capillary tube to heat the fluid to a suitable temperature for volatilizing the fluid therein. The volatilized fluid exits an outlet of the bent capillary tube 20, and the volatilized fluid forms an aerosol which can be inhaled by a person, drawing upon the mouthpiece 18.

The aerosol generator shown in FIG. 1 can be modified to utilize different fluid supply arrangements. For instance, the fluid source can comprise a delivery valve which delivers a predetermined volume of fluid to the bent capillary tube 20 and/or the bent capillary tube 20 can include one or more metering chambers of predetermined size to accommodate a predetermined volume of fluid to be volatilized during an inhalation cycle. In the case where the bent capillary tube 20 includes one or more metering chambers to accommodate a volume of fluid, the device can include a valve or valves downstream of the chamber(s) for preventing flow of the fluid beyond the chamber(s) during filling thereof. If desired, the chamber(s) can include a preheater arranged to heat fluid in the chamber(s) such that a vapor bubble expands and drives the remaining liquid from the chambers into the bent capillary tube 20. Details of such a preheater arrangement can be found in commonly owned U.S. Pat. No. 6,491,233, the disclosure of which is hereby incorporated by reference. Alternatively, fluid in the chamber(s) could be preheated to a set temperature below vapor bubble formation. If desired, the valve(s) could be omitted and the fluid source 12 can include a delivery arrangement such as one or more syringe pumps which supply a predetermined volume of fluid directly to the bent capillary tube 20. In the case where the bent tube is made of an electrically conductive material such as stainless steel, the heating arrangement can be a portion of the capillary tube defining bent capillary tube 20, arranged to volatilize the liquid in bent capillary tube 20. The sensor 15 can be omitted or bypassed in the case where the aerosol generator 10 is operated manually by a mechanical switch, electrical switch or other suitable technique. Although the aerosol generator 10 illustrated in FIG. 1 is useful for aerosolization of inhalable aerosols, such as drug or flavor bearing aerosols, the bent capillary tube can also be used to vaporize other fluids such as, for example, odorants.

A bent capillary tube aerosol generator may receive fluid flow from a single fluid source. A fluid, generally in the form of a pressurized liquid and/or predetermined volume of fluid from the same or separate fluid sources, enters through the inlets of the capillary tube and flows through the legs of the tube towards the outlet of the tube. A separate electrode is provided at each inlet end of the capillary tube. The portion of the capillary tube between the electrodes is heated as a result of the electrical current flowing through a portion of the tube between the electrodes, and the liquid entering the inlet ends is heated within the tube to form a vapor. As the vapor exits from the outlet of the capillary tube and comes into contact with the surrounding ambient air, the vapor forms an aerosol. If the liquid is a suspension, the aerosol can be formed from solids in the suspension. If the liquid is a solution of a condensable liquid, the aerosol can be formed from droplets of condensed vapor. If the outlet is smaller in cross-section that the internal diameter of the capillary tube, the aerosol can be formed from atomized liquid driven through the outlet by vaporized liquid.

Figure 2:
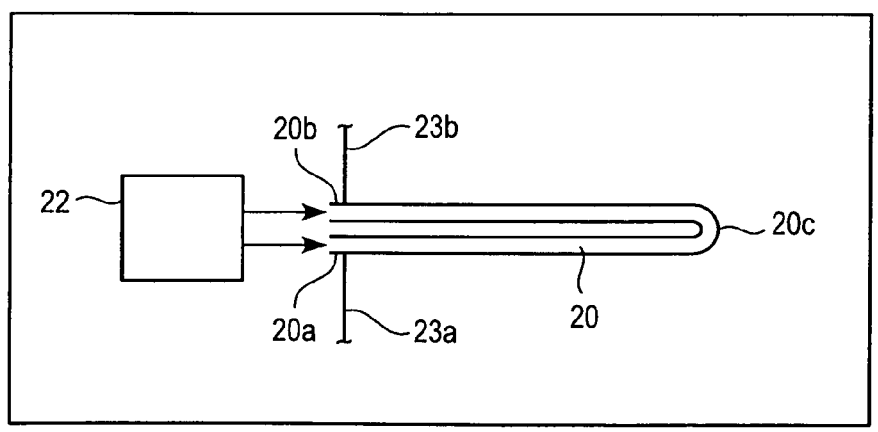
FIG. 2 is a schematic representation of a bent capillary tube portion of the device shown in FIG. 1.

As shown in FIG. 2, a fluid vaporizing device includes a capillary tube 20, with a fluid from a fluid source 22 passing through the capillary tube 20. The fluid enters the capillary tube 20 at first inlet end 20a and second inlet end 20b, and exits as a vapor from the outlet 20c of capillary tube 20. A first electrode 23a is connected near the inlet end 20a of capillary tube 20, and a second electrode 23b is connected near the inlet end 20b.

A liquid entering at the inlet 20a of capillary tube 20 and inlet 20b is heated as it passes through the capillary tube. Sufficient heat is input to the fluid passing through the tube to vaporize at least some of the fluid as it exits from the outlet 20c of the capillary tube. Again, while not illustrated but as indicated above, the aerosol generator may include more than one fluid source for each inlet of the bent capillary tube.

FIGS. 3a-b illustrate an enlarged view of the bent capillary tube 30. FIG. 3a provides a front view of the bent capillary tube 30, in which fluid enters at first inlet end 30a and second inlet end 30b, and exits as a vapor from the outlet 30c in a semicircular bend in capillary tube 30. A first electrode 33a is connected near the inlet end 30a of capillary tube 30, and a second electrode 33b is connected near the inlet end 30b. FIG. 3b illustrates a top view of the bent capillary tube, and FIG. 3c provides a magnified view of the outlet of the capillary tube.

Figure 4C:
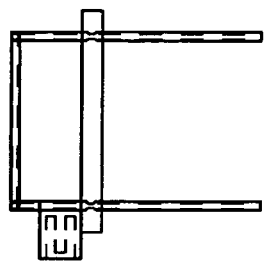
FIGS. 4a-c provide perspective views of the bent capillary tube connected to and extending through an electronics driver printed circuit card with a controller, with FIG. 4a providing a top view, FIG. 4b providing a front view, and FIG. 4c providing an end view.
Figure 4A:
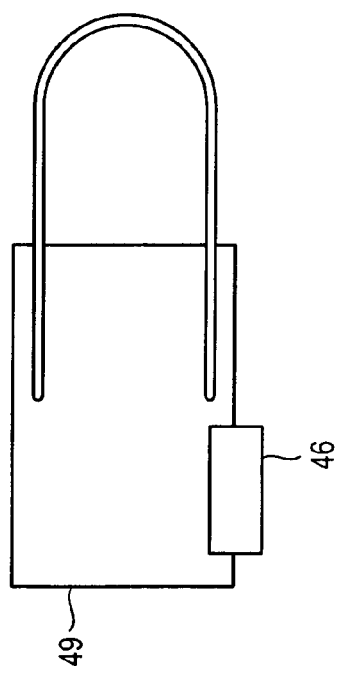
Figure 4B:
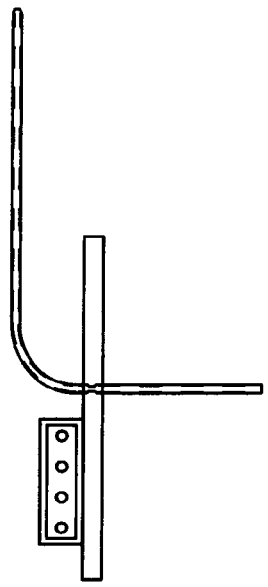

FIGS. 4a-c illustrate perspective views of the bent capillary tube. Specifically, FIG. 4a provides a top view of the bent capillary tube, which is connected to and extends through the electronics driver printed circuit card 49 with a controller 46, FIG. 4b provides a front view of the bent capillary tube, which is connected to the electronics driver printed circuit card and controller, and FIG. 4c provides an end view of the bent capillary tube, which is connected to the electronics driver printed circuit card and controller. The legs of the bent capillary tube are preferably connected to the electronics driver printed circuit card by a conductive adhesive, such as, for example, solder or conductive epoxy, allowing the electronics driver printed circuit card to supply electricity to the legs of the bent capillary tube to heat the bent capillary tube.

Figure 6:
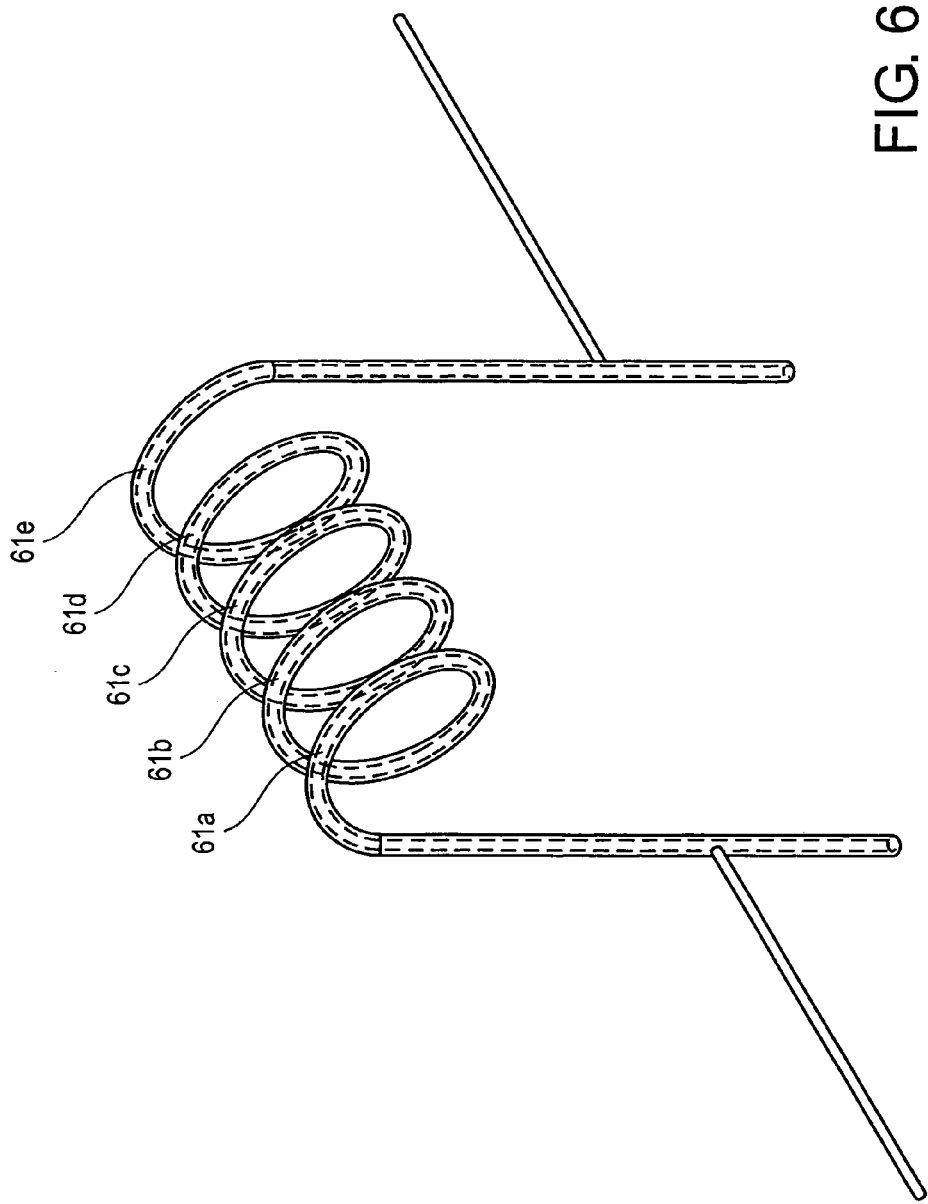
Figure 7:
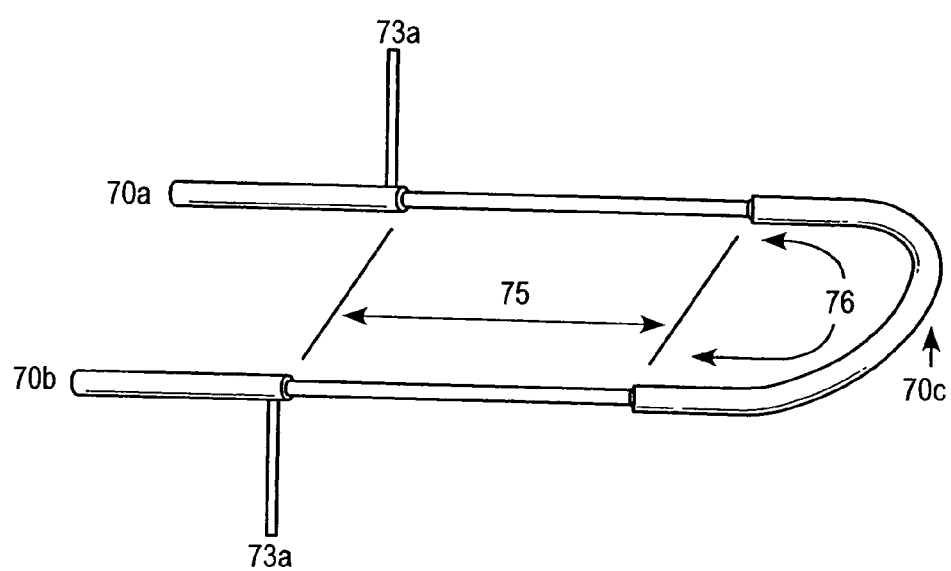
FIG. 7 shows an embodiment of a bent capillary tube having regions of reduced wall thickness located between the fluid inlets and the bend of the capillary tube.

Additional embodiments of the bent capillary tube are schematically shown with reference to FIGS. 5 and 6. The bent capillary tube of FIG. 5 includes multiple bends 51a, 51b, 51c, preferably have a single outlet along the centermost bend 51b. The bent capillary tube of FIG. 6 includes a coiled tube having multiple bends 61a, 61b, 61c, 61d, 61e, preferably have a single outlet in the centermost bend 61c.

The bent capillary tube arrangement is designed to accommodate a variety of liquid flow rates through the capillary tube, is highly energy efficient and provides a compact arrangement. In inhaler applications, the heating zones of the capillary tube can be 5 to 40 millimeters long, or more preferably 10 to 25 millimeters long, and the inner diameters of the tube can be 0.1 to 0.5 millimeters, or more preferably 0.1 to 0.2 millimeters. In implementing the capillary heater in an inhaler, the bent capillary tube arrangement is preferably insulated and/or isolated from ambient air and the vapor emitted from the capillary tube. For example, a body of insulating material could be used to support the bent capillary within a mouthpiece such that the vapor exiting the capillary tube does not contact the outer surface of the capillary tube.

The direction of discharge from the capillary is disclosed in FIG. 3 as being oriented in a direction within the general plane of the capillary away from the end of portions of the capillary. In the alternative, the discharge may instead be in a direction within the general plane of the capillary toward the end of portions of the capillary or in a direction outside of the general plane defined by the capillary, such as a direction that is orthogonal to the general plane defined by the capillary.

As shown in FIG. 7, a fluid vaporizing device preferably comprises a capillary tube, with a fluid from a fluid source entering the capillary tube at first inlet end **70*a* and second inlet end 70*b*, and exits as a vapor from the outlet 70*c* in a bend of the capillary tube. A first electrical power lead 73*a* is connected near the inlet end 70*a* of the capillary tube, and a second electrical power lead 73*b* is connected near the inlet end 70*b*. In the fluid region 75** of the capillary tube, the wall thickness of the capillary tube is preferably reduced in regions 75, as compared to the bend region 76 of the capillary tube. With this arrangement, it is possible to increase electrical resistance heating in regions 75 compared to the resistance heating in region 76 where less liquid is present.

While various embodiments have been described, it is to be understood that variations and modifications may be resorted to as will be apparent to those skilled in the art. Such variations and modifications are to be considered within the purview and scope of the claims appended hereto.

What is claimed is:

1. An aerosol generator, comprising:
    a single, continuous capillary tube, the capillary tube comprising at least one bend, fluid inlets, wherein the fluid inlets are located at ends of the capillary tube, regions of reduced wall thickness located between the fluid inlets and the bend, and an outlet along the bend; and
    first and second electrical leads, wherein an electrical connection between the first and second electrical leads is solely through a continuous length of the capillary tube, and wherein electrical resistive heating includes the outlet along the bend, and wherein volatilized fluid discharges from the outlet to form an aerosol.

2. The aerosol generator of claim 1, wherein the electrical resistance is increased in the regions of reduced wall thickness.

3. The aerosol generator of claim 1, wherein the capillary tube includes a first fluid inlet located at a first end and a second fluid inlet located at a second end of the capillary tube comprising the at least one bend, and wherein the outlet extends between an inner periphery and an outer periphery of the capillary tube.

4. The aerosol generator of claim 1, wherein the capillary tube comprises more than one bend, and wherein the capillary tube is 5 to 40 millimeters long and has an inner diameter of 0.1 to 0.5 millimeters.

5. The aerosol generator of claim 1, further comprising a source of liquid in fluid communication with the fluid inlets.

6. The aerosol generator of claim 1, wherein the capillary tube is 10 to 25 millimeters long and has an inner diameter of 0.1 to 0.2 millimeters, and wherein the capillary tube has a wall thickness of about 0.1 millimeters.

7. The aerosol generator of claim 1, wherein the regions of reduced wall thickness have a wall thickness of about 0.01 millimeters to 0.09 millimeters.

8. The aerosol generator of claim 1, wherein the regions of reduced wall thickness have a wall thickness of about 0.04 millimeters, and wherein the regions of reduced wall thickness are about 5.0 millimeters to about 7.0 millimeters in length.

9. The aerosol generator of claim 1, wherein the capillary tube includes two regions of reduced wall thickness.

10. The aerosol generator of claim 1, wherein the outlet is spaced apart from and in communication with the fluid inlets.

11. The aerosol generator of claim 1, wherein the outlet has a diameter approximately equal to an inner diameter of the capillary tube along the bend.

12. The aerosol generator of claim 1, wherein the first and second electrical leads are arranged near the fluid inlets.

13. An aerosol generator comprising:
    a single, continuous capillary tube comprising at least one bend, fluid inlets, regions of reduced wall thickness located between the fluid inlets and the bend, and an outlet along the at least one bend, the outlet having a diameter approximately equal to an inner diameter of the capillary tube along the at least one bend, and wherein the fluid inlets are located at ends of the capillary tube; and
    a heating mechanism which heats the capillary tube to a temperature sufficient to volatilize fluid in the capillary tube, the heating mechanism including first and second electrical leads, and wherein an electrical connection between the first and second electrical leads is solely through a continuous length of the capillary tube, and wherein electrical resistive heating includes the outlet along the bend.

14. The aerosol generator of claim 13, wherein the capillary tube is made of electrically resistive heating material, and wherein the electrical resistance is increased in the regions of reduced wall thickness, and the heating mechanism comprises a power supply and the first and second electrical leads attached to the capillary tube such that current passes along the bend and heats the capillary tube to the temperature sufficient to volatilize fluid in the capillary tube.

15. The aerosol generator of claim 14, wherein the regions of reduced wall thickness are located between the leads and the bend.

16. The aerosol generator of claim 13, further comprising a mouthpiece.

17. The aerosol generator of claim 13, further comprising a source of fluid in fluid communication with the fluid inlets.

18. A method for generating an aerosol, comprising the steps of:
    supplying fluid to an aerosol generator comprising a single, continuous capillary tube comprising at least one bend, first and second fluid inlets, regions of reduced wall thickness located between the fluid inlets and the bend, and an outlet along the bend, and wherein the first and second fluid inlets are located at ends of the capillary tube; and
    heating the capillary tube to heat the fluid to a temperature sufficient to volatilize the fluid to form a volatilized fluid, such that the volatilized fluid discharges from the outlet of the capillary tube to form the aerosol, wherein the heating includes first and second electrical leads, and wherein an electrical connection between the first and second electrical leads is solely through a continuous length of the capillary tube, and wherein electrical resistive heating includes the outlet along the bend.

19. The method of claim 18, wherein the outlet is equidistant from the first and second fluid inlets.

20. The method of claim 18, wherein the fluid is supplied to the first and second fluid inlets at different flow rates.

21. The method of claim 18, wherein different fluids are supplied to the first and second fluid inlets.

22. The method of claim 18, wherein a liquid is supplied to the first fluid inlet and a gas is supplied to the second fluid inlet.

23. The method of claim 18, wherein fluid supplied to the capillary tube comprises a tobacco extract, a medicament, a fuel, water, a flavorant or a carrier.

24. An aerosol generator comprising:
    a single, continuous capillary tube, the capillary tube comprising a single bend, a first fluid inlet located at a first end and a second fluid inlet located at a second end of the capillary tube comprising the single bend, regions of reduced wall thickness located between the first and second fluid inlets and the single bend, a single, common outlet along the single bend, and wherein the single, common outlet is spaced apart from and in communication with the first and second fluid inlets, and wherein volatilized fluid discharges from the single, common outlet to form an aerosol;

first and second electrical leads arranged near the first and second fluid inlets, wherein an electrical connection between the first and second electrical leads is solely through a continuous length of the capillary tube, and wherein electrical resistive heating includes the outlet along the single bend; and a source of liquid in fluid communication with the first and second fluid inlets.

25. An aerosol generator in the form of a single, continuous capillary tube, the capillary tube comprising at least one bend, fluid inlets, regions of reduced wall thickness located between the fluid inlets and the bend, and an outlet along the bend, wherein volatilized fluid discharges from the outlet to form an aerosol, and wherein the fluid inlets are located at ends of the capillary tube, and wherein the capillary tube comprises multiple bends, and the outlet is a single outlet along a centermost bend.

26. An aerosol generator, comprising:

a single, continuous capillary tube, the capillary tube including fluid inlets located at ends of the capillary tube and an outlet; and first and second electrical leads, wherein an electrical connection between the first and second electrical leads is solely through a continuous length of the capillary tube, and wherein electrical resistive heating includes the capillary tube at the outlet and a volatilized fluid discharges from the outlet to form an aerosol.

* * * * *